(12) United States Patent
Du et al.

(10) Patent No.: US 7,671,232 B2
(45) Date of Patent: Mar. 2, 2010

(54) METHOD FOR FABRICATING A HIGH SPECIFIC SURFACE AREA MESOPOROUS ALUMINA

(75) Inventors: Tz-Bang Du, Dongshan Township, Yilan County (TW); Yung-Chan Lin, Lujhou (TW); Bor-Wen Chen, Hsinchu (TW); Shyue-Ming Jang, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 1029 days.

(21) Appl. No.: 11/242,836

(22) Filed: Oct. 5, 2005

(65) Prior Publication Data

US 2006/0116527 A1 Jun. 1, 2006

(30) Foreign Application Priority Data

Nov. 26, 2004 (TW) .............................. 93136490 A

(51) Int. Cl.
 *C07C 69/34* (2006.01)
(52) U.S. Cl. ..................................................... 560/197
(58) Field of Classification Search ........................ None
 See application file for complete search history.

(56) References Cited

U.S. PATENT DOCUMENTS

| 3,268,571 A * | 8/1966 | Mitsch .......................... 558/54 |
| 5,565,081 A | 10/1996 | Krespan et al. |
| 2003/0135067 A1 | 7/2003 | Okazoe et al. |

FOREIGN PATENT DOCUMENTS

TW 200422258 11/2004

OTHER PUBLICATIONS

Mironov et al, ARKIVOC, published on Web Feb. 19, 2005, pp. 95-127.*

* cited by examiner

*Primary Examiner*—Paul A Zucker
(74) *Attorney, Agent, or Firm*—Bacon & Thomas, PLLC

(57) ABSTRACT

A method for fabricating a high specific surface area mesoporous alumina is disclosed, which includes the following steps: (a) providing a water solution containing an aluminum salt and a fluoro-surfactant; (b) adding concentrated hydrochloric acid to adjust the PH value of the solution to about 6.0 to 8.0; (c) aging the solution at 70° C. to 110° C. for 12 to 20 hours; (d) washing the precipitate with water; (e) washing the precipitate with an organic solvent; (f) drying the precipitate; and (g) sintering the precipitate in a furnace of 500° C. to 1000° C.

7 Claims, No Drawings

METHOD FOR FABRICATING A HIGH SPECIFIC SURFACE AREA MESOPOROUS ALUMINA

BACKGROUND OF THE INVENTION

1. Field of the Invention

The present invention relates to a method for fabricating an alumina, and more particularly, a method for fabricating a high specific surface area mesoporous alumina.

2. Description of the Related Art

According to pore sizes, porous materials are generally classified into microporous materials with a pore size less than 2 nm, mesoporous materials with a pore size between 2 nm and 50 nm, and macroporous materials with a pore size more than 50 nm. However, because the pore diameters of microporous materials are too small and the pores of macroporous materials are not uniformly distributed, mesoporous materials without the above defects are widely used as catalysts, carriers for catalysts, gas adsorptive agents, filter materials, etc. Among the mesoporous materials, mesoporous alumina is easy to obtain and quite cheap so that it is used a great deal. Besides, with the greater needs for specialty chemicals, mesoporous alumina has a quite high profit as a high unit priced fine-purification, adsorptive material.

The conventional method for manufacturing a mesoporous alumina is mainly divided by starting material into a more expensive group of aluminum alkoxide and a cheaper group of aluminum salts such as aluminum nitrate and aluminum sulfate. Taking aluminum alkoxide as anstarting material, the method for fabricating a mesoporous alumina can produce a porous alumina with its porous diameter maintained on 11 nm. However, the cost of aluminum alkoxide is high, and its specific surface area would be less than 150 m$^2$/g when sintering at 1030° C. with the result that it would be limited in practice.

Taking cheaper the aluminum salts, such as aluminum nitrate, aluminum sulfate, aluminum chloride and sodium aluminate, as thestarting material, the cost could be lowered, but the mesoporous alumina obtained by the conventional method has many defects in its porous characteristics. For example, the distribution of the pores is too wide to apply to a fine-purification system that requires high operating demands; the temperature for sintering is too low to use in petroleum cracking; the pore volume is too small, etc. Although the conventional method could overcome the above limitations by adding a PEO surfactant as a structure directing material, the pore volume of its mesoporous product is still too small.

SUMMARY OF THE INVENTION

The present invention provides a fluoro-surfactant of formula (I),

$$H(CF_2)_mOOC(CH_2)_nCOO(CF_2)_mH \qquad \text{formula (I)}$$

Wherein m and n are integers between 1 and 10.

The present invention also provides a method for manufacturing a fluoro-surfactant of formula (I), which includes the following steps: (A) providing a dicarboxylic acid of the following formula (II) and a fluoroalcohol of the following formula (III); (B) dissolving the dicarboxylic acid, the fluoroalcohol, and a p-toluenesulfonic acid in an organic solvent to form a solution, wherein the molar number of the fluoroalcohol is over twice the molar number of the dicarboxylic acid and the p-toluenesulfonic acid acts as a catalyst; (C) refluxing and heating the solution to proceed the reaction; and (D) removing the solvent from the solution by evaporation to obtain the product; wherein m and n are integers between 1 and 10.

$$HOOC(CH_2)_nCOOH \qquad \text{formula (II)}$$

$$H(CF_2)_mOH \qquad \text{formula (III)}$$

Furthermore, the present invention provides a method for manufacturing a high specific surface area alumina, which includes the following steps: (A) providing a fluoro-surfactant of formula (I) or that of the following formula (IV); (B) dissolving an aluminum salt and the fluoro-surfactant in water to form a solution, wherein the molar ration between the fluoro-surfactant and the aluminum salt is 0.002-0.2:1; (C) adjusting the PH value of the solution to 6.0-8.0, by which a precipitate is produced in the solution; (D) heating the solution at the temperature of 80° C.-100° C. to proceed the aging; (E) washing the precipitate with water; (F) washing the precipitate with an organic solvent that can be miscible with water in order to replace the water content of the precipitate; (G) drying the precipitate; and (H) sintering the precipitate at the temperature of 400° C.-1100° C.

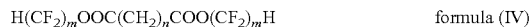

$$H(CF_2)_mOOC(CH_2)_nCOO(CF_2)_mH \qquad \text{formula (IV)}$$

Wherein m and n are integers between 1 and 10. In this way, the method of the present invention could reduce the use of the structure directing materials and also lower the cost. Besides, the method of the present invention could produce a mesoporous alumina of high specific surface area and homogeneous distribution of pore size.

In the method for fabricating a fluoro-surfactant of the present invention, the dicarboxylic acid can be any conventional organic dicarboxylic acid.

Preferably, the dicarboxylic acid is malonic acid and acetic anhydrate. In the method for fabricating a fluoro-surfactant of the present invention, the fluoroalcohol can be any conventional fluoroalcohol. Preferably, the fluoroalcohol is 2,2,3,3-tetrafluoro-1-propanol or 2,2,3,3,4,4,5,5-octafluoro-1-pentanol. In the method for fabricating a fluoro-surfactant of the present invention, the step (C) is reacted by refluxing and heating preferably for 6 to 9 hours to gain vaporized liquid with theoretical weight of water up to 80-95%. The method for fabricating a fluoro-surfactant of the present invention can selectively further comprise step (D') to extract the product with another organic solvent, then removing the organic solvent through evaporation to purify the product, and it is preferable to evaporate the organic solvent by reducing pressure in the step (D').

In the method for fabricating a high specific surface area alumina of the present invention, the aluminum salt can be any conventional aluminum salt. Preferably, the aluminum salt is aluminum nitrate, aluminum sulfate, aluminum chloride or sodium aluminate. In the method for fabricating a high specific surface area alumina of the present invention, the fluoro-surfactant can be any conventional fluoro-surfactant. Preferably, the fluoro-surfactant is Bis(2,2,3,3-tetrafluoropropanyl)Malonate (BTFM), Bis(2,2,3,3,4,4,5,5-octafluoropentyl)Malonate (BOFM) or 2,2,3,3-tetrafluoropropanyl acetate (TFPA). In the method for fabricating a high specific surface area alumina of the present invention, the PH value of the solution can be adjusted by any conventional method in step (C), and it is preferable to adjust the PH value by adding concentrated hydrochloric acid. In the method for fabricating a high specific surface area alumina of the present invention, any organic solvent miscible with water can be used in step (F), and preferably, a solution with low boiling point and low surface tension is used. In the method for fabricating a high specific surface area alumina of the present invention, any drying method, such as drying by heating in an oil-bathed pot or drying by a vacuum oven, can be used in step (G). In the method for fabricating a high specific surface area alumina of the present invention, the time for aging in step (D) is between 12 and 20 hours. In the method for fabricating a high specific surface area alumina of the present invention, the time for sintering is between 4 and 8 hours.

DETAILED DESCRIPTION OF THE PREFERRED EMBODIMENTS

EXAMPLE 1-1

Synthesis of fluoro-surfactant (BTFM)

30.2 grams of 2,2,3,3-tetrafluoro-1-propanol, 10 grams of malonic acid and 7.31 grams of p-toluenesulfonic acid are added into 250 ml of toluene. The mixture is reacted under reflux for 8 hours and then the vaporized liquid with theoretical weight of water up to 90% is collected by using a Dean-Stark trap. 15 grams of 2,2,3,3-tetrafluoro-1-propanol is added again and refluxed for 4 hours. The solvent is evaporated and then extracted three times with ethyl acetate. The ethyl acetate is removed by reduced pressure steam with the outer temperature of 115° C. and 0.2 torr to obtain 23.3 grams of Bis(2,2,3,3-tetrafluoropropanyl)Malonate (BTFM).
$^1$H NMR (300 MHz, CDCl$_3$; ppm): δ 3.56 (s, 2H), 4.54 (t, J=12.6 Hz, 4H), 5.86 (tt, J=52.9 Hz, J=3.6 Hz, 2H)○ $^{13}$C NMR (75 MHz, CDCl$_3$, ppm): δ 39.9 (s), 60.3 (t, J=28.9 Hz), 109.2 (tt, J=248.2 Hz, J=35.9 Hz), 113.9 (tt, J=248.3 Hz, J=27.8 Hz), 164.5 (s)○

EXAMPLE 1-2

Synthesis of fluoro-surfactant (BOFM)

45.0 grams of 2,2,3,3,4,4,5,5-octafluoro-1-pentanol, 10 grams of malonic acid and 7.31 grams of p-toluenesulfonic acid are added into 200 ml of toluene. The mixture is reacted under reflux for 4 hours and then the vaporized liquid with theoretical weight of water up to 90% is collected by using a Dean-Stark trap. The solvent is evaporated and then extracted three times with ethyl acetate. The ethyl acetate is removed by reduced pressure steam with the outer temperature of 115° C. and 0.2 torr to obtain 45.1 grams of Bis(2,2,3,3,4,4,5,5-octafluoropentyl)Maleate (BOFM).
$^1$H NMR (400 MHz, CDCl$_3$ ppm: δ 3.58 (s, 2H), 4.64 (t, J=13.6 Hz, 4H), 6.02 (tt, J=52.0 Hz, J=5.4 Hz, 2H)○ $^{13}$C NMR (75 MHz, CDCl$_3$, ppm): δ 40.0 (s), 60.3 (t, J=26.9 Hz), 107.8 (tt, J=253.1 Hz, J=30.8 Hz), 110.2 (m), 114.4 (tt, J=256.4 Hz, J=30.5 Hz), 164.2 (s)○

EXAMPLE 1-3

Synthesis of fluoro-surfactant (TFPA)

26.4 grams of 2,2,3,3-tetrafluor-1-propanol, 30.6 grams of acetic anhydrate and 15.2 grams of toluol-4-sulfonic acid monohydrate are reacted at the outer temperature of 120° C. for 12 hours and then are cooled down to room temperature. The product is washed with 100 ml of ethyl ether and 50 ml of pure water for three times. The ethyl ether layer is then distilled. The outer temperature is set at up to 90° C. When there is no distillation any more, the product is washed with 100 ml of pure water for three times to obtain 14.67 grams of 2,2,3,3-tetrafluoropropanyl acetate (TFPA).
$^1$H NMR (300 MHz, CDCl$_3$, PPM): δ 2.06 (s, 3H), 4.39 (t, J=13.2 Hz, 2H), 5.83 (tt, J=53.6 Hz, J=3.4 Hz, 1H)○

The lipohydrophilic part of the fluoro-surfactant of the present invention is a carbon-fluorine chain that has a better hydrophobicity than general carbonhydrogen chain.

In the method for manufacturing a mesoporous alumina of the present invention, a surfactant of fluoro dicarboxylic acid or fluoro carboxylic acid can be used as the structure directing material. In this embodiment, the fluoro dicarboxylic acid such as BTFM and BOFM and the fluoro carboxylic acid such as TFPA are used respectively as the structure directing material to prepare the mesoporous alumina.

EXAMPLE 2-1

Preparation of Mesoporous Alumina with BTFM Surfactant 10 grams of sodium aluminate is added into 100 ml of water and stirred to dissolve. 0.1 gram of BTFM surfactant is added and stirred to mix with the solution. Concentrated hydrochloric acid is dripped into the solution until its PH value is 7. Stirring is then stopped and the beaker is moved into an oil-bathed pot to age at the outer temperature of 90° C. for 16 hours. The product is washed and stirred with 300 ml of pure water and then isolated centrifugally for three times. Following the above step, the product is then washed with 300 ml of methanol for three times. The resulting product is put into the oil-bathed pot and dried at 90° C. for 2 hours. The product is moved into a vacuum oven and dried at 90° C. for 16 hours. The dried product is ground and then moved into a furnace to sinter at 1000° C. for 5 hours to obtain a mesoporous alumina the porous volume of which is 0.76 cm$^3$/g, the pore diameter of which is 17.8 nm and the specific surface area of which is 168 m$^2$/g.

EXAMPLE 2-2

Preparation of Mesoporous Alumina with BOFM Surfactant 10 grams of sodium aluminate are added into 100 ml of water and are stirred to dissolve. 0.5 gram of BOFM surfactant is added and stirred to mix with the solution. Concentrated hydrochloric acid is dripped into the solution until its PH value is 7. Stirring is stopped and the beaker is moved into an oil-bathed pot to age at the outer temperature of 90° C. for 16 hours. The product is washed and stirred with 300 ml of pure water and then isolated centrifugally for three times. By the same way, the product is washed with 300 ml of methanol for three times. The resulting product is put into the oil-bathed pot and dried at 90° C. for 2 hours. The product is moved into a vacuum oven and dried at 110° C. for 16 hours. The dried product is ground and then moved into a furnace to sinter at 1000° C. for 5 hours to obtain a mesoporous alumina the porous volume of which is 0.66 cm$^3$/g, the pore diameter of which is 13.7 nm and the specific surface area of which is 192.2 m$^2$/g.

EXAMPLE 2-3

Preparation of Mesoporous Alumina with TFPA Surfactant 10 grams of sodium aluminate is added into 100 ml of water and stirred to dissolve. 2.5 grams of TFPA surfactant is added and stirred to mix with the solution. Concentrated hydrochloric acid is dripped into the solution until its PH value is 7. Stirring is stopped and the beaker is moved into an oil-bathed pot to age at the outer temperature of 90° C. for 16 hours. The product is washed and stirred with 300 ml of pure water and then isolated centrifugally for three times. By the same way, the product is washed with 300 ml of methanol for three times. The resulting product is put into the oil-bathed pot and dried at 90° C. for 2 hours. The product is moved into a vacuum oven and dried at 110° C. for 16 hours. The dried product is ground and then moved into a furnace to sinter at 1000° C. for 5 hours to obtain a mesoporous alumina the porous volume of which is 1.05 cm$^3$/g, the pore diameter of which is 15.8 nm and the specific surface area of which is 257 m$^2$/g.

EXAMPLE 2-4

Preparation of Mesoporous Alumina with BTFM Surfactant and by Sintering at 500° C.

10 grams of sodium aluminate is added into 100 ml of water and stirred to dissolve. 0.5 gram of BTFM surfactant is added and stirred to mix with the solution. Concentrated hydrochloric acid is stirred into the solution until its PH value is 7. Stirring is stopped and the beaker is moved into an oil-bathed pot to age at the outer temperature of 90° C. for 16 hours. The product is washed and stirred with 300 ml of pure water and then isolated centrifugally for three times. By the same way, the product is washed with 300 ml of methanol for three times. The resulting product is put into the oil-bathed pot and dried at 90° C. for 2 hours. The product is moved into a vacuum oven and dried at 110° C. for 16 hours. The dried product is ground and then moved into a furnace to sinter at 500° C. for 5 hours to obtain a mesoporous alumina the porous volume of which is 0.68 cm3/g, the pore diameter of which is 6.1 nm and the specific surface area of which is 426 m$^2$/g.

The method for fabricating a high specific surface area alumina of the present invention adopts a method of solvent replacement to remove the water from the hydrated alumina by using a solvent miscible with water, such as methanol. This method can prevent a result in which the pores would collapse to make the reduction of the porous volume while drying the precipitate due to its high hydrous capacity and when there are no structure directing materials. Besides, in comparison with conventional ways to take PEO as structure directing material, the fluoride-surfactant used in the present invention the lipohydrophilic term of which is a carbon chain containing fluorine has a better hydrophobicity than a general carbon chain containing hydrogen. Therefore, it can efficiently form microcells to support the pores, reduce the amount of the structure directing materials, and diminish the resistance of draining and drying. The conventional technology obtains a mesoporous alumina that has specific surface area of 166.5 m$^2$/g and porous volume of 0.79 cm$^3$/g with a surfactant of a molar ratio of 0.15 and sintering at 900° C. However, the present embodiment only uses a surfactant of a molar ratio of 0.12 sintered at 1000° C. to gain a mesoporous alumina of higher specific surface area. Further, the present invention can also obtain a mesoporous alumina with a specific surface area of 426 m$^2$/g by using few surfactants of a molar ratio of 0.012 sintered at 500° C. The resulted specific surface area is much higher than that of the product made by conventional surfactant of molar ration of 0.4 sintered at the same temperature. In other words, the method for fabricating a high specific surface area alumina of the present invention improves a lot the use of a surfactant and the porous characteristics of the product.

In addition, measured by BET, the distribution of the pores is more concentrated than ever before, i.e., the porous diameter of the mesoporous alumina prepared by the present embodiment ranges from 2 to 20 nm.

COMPARATIVE EXAMPLE 1

Preparation of Mesoporous Alumina without Adding Surfactant 10 grams of sodium aluminate is added into 100 ml of water and stirred to dissolve. Concentrated hydrochloric acid is dripped into the solution until its PH value is 7. Stirring is stopped and the beaker is moved into an oil-bathed pot to age at the outer temperature of 90° C. for 16 hours. The product is washed and stirred with 300 ml of pure water and then isolated centrifugally for three times. By the same way, the product is washed with 300 ml of methanol for three times. The resulting product is put into the oil-bathed pot and dried at 90° C. for 2 hours. The product is moved into a vacuum oven and dried at 110° C. for 16 hours. The dried product is ground and then moved into a furnace to sinter at 1000° C. for 5 hours to obtain a mesoporous alumina the porous volume of which is 0.32 cm$^3$/g, the pore diameter of which is 15.0 nm and the specific surface area of which is 81.9 m$^2$/g.

The steps of comparative example 1 are identical to those of the examples, except that there is no fluoride-surfactant added. However, the specific surface area and the porous volume of the mesoporous alumina provided by comparative example 1 are much smaller than those of the examples. As a result, the fluoride-surfactant of the present invention does help to support the porous microcells.

COMPARATIVE EXAMPLE 2

Preparation of Mesoporous Alumina without Washing Procedure and Surfactant 10 grams of sodium aluminate is added into 100 ml of water and stirred to dissolve. Concentrated hydrochloric acid is dripped into the solution until its PH value is 7. Stirring is stopped and the beaker is moved into an oil-bathed pot to age at the outer temperature of 70° C. for 5.5 hours. The product is moved into a vacuum oven and dried at 70° C. for 15 hours. The dried product is ground and then moved into a furnace to sinter at 1000° C. for 5 hours to obtain a mesoporous alumina the porous volume of which is 0.096 cm$^3$/g, the pore diameter of which is 10.9 nm and the specific surface area of which is 35.1 m$^2$/g.

Comparing the comparative example 2 with comparative example 1, no surfactants are added and all manufacturing conditions are the same, except that the mesoporous alumina of comparative example 2 is prepared without the washing procedure. However, the porous volume, porous diameters and the specific surface area of the comparative example 2 are smaller than those of the comparative example 1. As a result, the method for replacing water with organic solvent miscible with water used in the manufacturing method of the present invention can prevent the pores from collapsing, and so prevent reduction of the porous volume due to dryness.

Fine-Purification Test

Taking the mesoporous alumina obtained by the present invention and mesoporous alumina AC61 to proceed a liquid crystal adsorptive purification. The present invention measures the original specific resistance of recycled liquid crystal. Then, the recycled liquid crystal is mixed with 5 wt % of adsorptive materials and the mixture is stirred. After filtering with 0.2 μm PTFE film, the specific resistance of the adsorptive purified liquid crystal is measure to obtain a liquid crystal specific resistance, as shown in Table 1. In Table 1, it is obvious that the method for manufacturing mesoporous alumina of the present invention has better fine-filtering and adsorptive characteristics than that of the merchandise mesoporous alumina.

TABLE 1

| Adsorptive Material | Original Resistance | Adsorptive Purification by 5 wt % |
|---|---|---|
| AC61 | $3.6 \times 10^{12}$ Ωcm | $5.9 \times 10^{12}$ Ωcm |
| Alumina of the present invention | $1.8 \times 10^{12}$ Ωcm | $2.9 \times 10^{13}$ Ωcm |

Although the present invention has been explained in relation to its preferred embodiments, it is to be understood that many other possible modifications and variations can be made without departing from the scope of the invention as hereinafter claimed.

What is claimed is:

1. A fluoro-surfactant of the following formula (I): $H(CF_2)_m OOC(CH_2)_n COO(CF_2)_m H$ formula (I) wherein m and n are integers between 1 and 10; the fluro-surfactant is Bis(2,2,3,3-tetrafluropropanyl) Malonate (BTFM) or Bis(2,2,3,3,4,4,5,5-octafluoropentyl) Malonate (BOFM).

2. A method for fabricating a fluoro-surfactant of the following formula (I), which contains steps of:

$H(CF_2)_m OOC(CH_2)_n COO(CF_2)_m H$      formula (I)

(A) providing a dicarboxylic acid of the following formula (II) and a fluoroalcohol of the following formula (III):

$HOOC(CH_2)_n COOH$      formula (II)

$H(CF_2)OH$      formula (III)

(B) dissolving said dicarboxylic acid, said fluoroalcohol, and a p-toluenesulfonic acid in an organic solvent to form a solution, wherein the molar number of said fluoroalcohol is over twice the molar number of said dicarboxylic acid and said p-toluenesulfonic acid acts as a catalyst;

(C) refluxing and heating said solution to proceed the reaction; and (D) removing the solvent from said solution by evaporation to obtain the product;

wherein m and n are integers between 1 and 10.

3. The method for fabricating a fluoro-surfactant as claimed in claim 2, wherein said dicarboxylic acid is malonic acid or acetic anhydrate.

4. The method for fabricating a fluoro-surfactant as claimed in claim 2, wherein said fluoroalcohol is 2,2,3,3-tetrafluoro-1-propanol or 2,2,3,3,4,4,5,5-octafluoro-1-pentanol.

5. The method for fabricating a fluoro-surfactant as claimed in claim 2, wherein said step (C) is reacted by refluxing and heating for 6 to 9 hours to gain vaporized liquid with theoretical weight of water up to 80-95%.

6. The method for fabricating a fluoro-surfactant as claimed in claim 2 further comprising a step (D') in which to extract the product with another organic solvent and then removing said organic solvent through evaporation to purify the product.

7. The method for fabricating a fluoro-surfactant as claimed in claim 6, wherein said organic solvent is evaporated by reducing pressure in said step (D').

* * * * *